United States Patent
Kumamoto et al.

(10) Patent No.: US 6,673,844 B2
(45) Date of Patent: Jan. 6, 2004

(54) WARMING COMPOSITION

(75) Inventors: Hiroyasu Kumamoto, Tokyo (JP); Hideaki Ohta, Tokyo (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/006,119

(22) Filed: Dec. 10, 2001

(65) Prior Publication Data

US 2002/0142015 A1 Oct. 3, 2002

(30) Foreign Application Priority Data

Dec. 12, 2000 (JP) .................................. P. 2000-376813

(51) Int. Cl.[7] ...................... A61K 31/11; A61K 31/045; A61K 47/11; A61K 7/00
(52) U.S. Cl. ...................... 514/699; 514/693; 514/729; 514/730; 424/439; 424/401
(58) Field of Search ................. 424/439, 401; 514/699, 693, 729, 730

(56) References Cited

U.S. PATENT DOCUMENTS

| 5,545,424 | A |   | 8/1996  | Nakatsu et al. |
| 5,753,609 | A | * | 5/1998  | Nakatsu et al. ............... 512/8 |
| 6,306,429 | B1 | * | 10/2001 | Bealin-Kelly ............... 424/439 |

FOREIGN PATENT DOCUMENTS

JP    2000-26268    1/2000

* cited by examiner

Primary Examiner—Sreeni Padmanabhan
Assistant Examiner—Jennifer Kim
(74) Attorney, Agent, or Firm—Sughrue Mion, PLLC

(57) ABSTRACT

A warming composition which produces an excellent warming effect of long duration with no or little skin irritation, a fragrance composition comprising the warming composition, and cosmetics, toiletries, bath additives, and pharmaceuticals containing the warming composition or the fragrance composition.

6 Claims, No Drawings

WARMING COMPOSITION

FIELD OF THE INVENTION

This invention relates to a warming composition which produces an excellent warming effect of long duration with no or little skin irritation, a fragrant composition comprising the warming composition, and cosmetics, toiletries, bath additives, and pharmaceuticals containing the warming composition or the fragrance composition.

BACKGROUND OF THE INVENTION

Substances which are known to provide a sensation of warmth on application and called "warming agents" include polyhydric alcohols, capsicum (red pepper) powder, a capsicum tincture, capsicum extract, capsaicin, homocapsaicin, homodihydrocapsaicin, nonanoyl vanillyl amide, nonanoic acid vanillyl ether, vanillyl alcohol alkyl ether derivatives (JP-A-57-9729), such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron.

These warming agents are added either as such or in the form of a fragrance composition to various products to produce a warming effect. However, the known warming agents often cause strong skin irritation or exhibit insufficient warming effects, and those having high warming effects are of short duration or, when used in a reduced amount, have insufficient warming effects or an insufficient duration of effect.

An object of the present invention is to provide a warming composition which is freed of these problems, i.e., causes no or little skin irritation and exhibits an excellent and long-lasting warming effect in a small amount.

Another object of the present invention is to provide a fragrance composition which causes no or little skin irritation and imparts a long-lasting warming effect when added in a small amount.

Still another object of the invention is to provide cosmetics, toiletries, bath additives and pharmaceuticals which contain the warming composition or the fragrance composition and exhibit excellent and long-lasting warming effects.

SUMMARY OF THE INVENTION

As a result of extensive investigations, the inventors have found that a combination of (A) a compound or a composition that has been known as a cooling agent (hereinafter inclusively referred to as a cooling agent) and a small amount of a compound represented by formula (I) (B) and/or (C) a compound or a composition that has been known as a warming agent (hereinafter inclusively referred to as a warming agent) produces such a warming effect as is never expected from each of the components used alone and as lasts as long as 3 hours or even more, and, when added to a product, exhibits an appreciable warming effect in such a low concentration at which each component would not stimulate individually, making it possible to produce a warming effect with no skin irritation that has not heretofore been attained.

The present invention provides a warming composition comprising (A) a cooling agent and (B) a compound represented by formula (I):

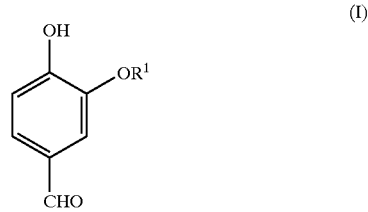

wherein $R^1$ represents a hydrogen atom, a methyl group or an ethyl group.

The present invention provides a warming composition comprising (A) a cooling agent and (C) a warming agent.

The present invention provides a warming composition comprising (A) a cooling agent, (B) a compound represented by formula (I), and (C) a warming agent.

The present invention also provides a fragrance composition comprising any of the above-described warming compositions.

The present invention also provides cosmetics, toiletries, bath additives or pharmaceuticals comprising any of the above-described warming compositions or the above-described fragrance composition.

In the present invention, a combination of a cooling agent and at least one of a warming agent and a specific compound produces an appreciable warming effect at such a low concentration at which each component alone is ineffective. The warming effect of the warming composition lasts for a long period of time that has not been thought. The warming composition is unlike conventional ones in that when it is applied to one's sole, the warming effect is also produced in her or his back, etc.

DETAILED DESCRIPTION OF THE INVENTION

The warming composition of the present invention comprises (A) a cooling agent and at least one of (B) a compound represented by formula (I) and (C) a warming agent.

The cooling agent as component (A) can be any compound or composition known as a cooling agent. Typical examples of the cooling agents which can be used in the present invention include:

(1) a compound represented by formula (II):

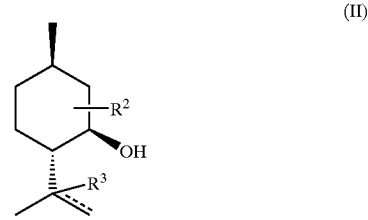

wherein $R^2$ and $R^3$ each represent a hydrogen atom or a hydroxyl group (═ represents a single bond or a double bond, the same definition applies hereinafter), (2) a compound represented by formula (III):

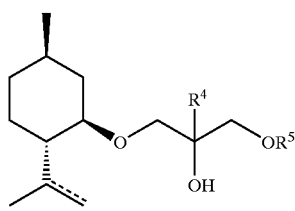

(III)

wherein $R^4$ represents a hydrogen atom or a methyl group; $R^5$ represents a hydrogen atom, a lower alkyl group or a 2-alkoxyethyl group,
(3) a compound represented by formula (IV):

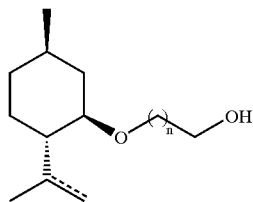

(IV)

wherein n represents an integer of 1 to 10,
(4) a compound represented by formula (V):

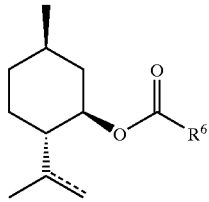

(V)

wherein $R^6$ represents a hydrogen atom, a straight-chain or branched alkyl or alkenyl group, or a straight-chain or branched hydroxyalkyl group,
(5) l-menthylacetic acid N-ethylamide, and (6) N,2,3-trimethyl-2-(1-methylethyl)-butanamide.

Specific examples of the cooling agents which are preferably used in the invention include, but are not limited to, menthol, isopulegol, 3-(l-menthoxy)propane-1,2-diol, 3-(l-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint (*Mentha arvensis*) oil, peppermint oil, menthone, menthone glycerol ketal, menthyl lactate, 3-(l-menthoxy)ethan-1-ol, 3-(l-menthoxy)propan-1-ol, 3-(l-menthoxy)butan-1-ol, l-menthylacetic acid N-ethylamide, l-menthyl-4-hydroxypentanoate, l-menthyl-3-hydroxybutyrate, N,2,3-trimethyl-2-(1-methylethyl)-butanamide, and spearmint oil.

Of these cooling agents preferred are 3-(l-menthoxy)propane-1,2-diol, 3-(l-menthoxy)-2-methylpropane-1,2-diol, p-menthane-3,8-diol, 3-(l-menthoxy)ethan-1-ol, 3-(l-menthoxy)propan-1-ol, and 3-(l-menthoxy)butan-1-ol. Still preferred are 3-(l-menthoxy)propane-1,2-diol and 3-(l-menthoxy)-2-methylpropane-1,2-diol.

Of the compounds represented by formula (I) as component (B) the compound in which $R^1$ is a methyl group, i.e., vanillin is preferred.

The warming agent as component (C) includes, but is not limited to,
(i) vanillyl alcohol, vanillyl alkyl or alkenyl ethers represented by formula (VI):

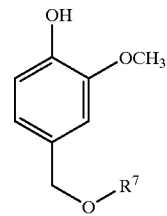

(VI)

wherein $R^7$ represents a hydrogen atom or a straight chain or branched alkyl or alkenyl group having 1 to 10 carbon atoms, preferably 1 to 6 carbon atoms,
such as vanillyl ethyl ether, vanillyl propyl ether, vanillyl butyl ether, vanillyl pentyl ether, and vanillyl hexyl ether;
(ii) vanillin propylene glycol acetal;
(iii) ethylvanillin propylene glycol acetal;
(iv) compounds represented by formula (VII):

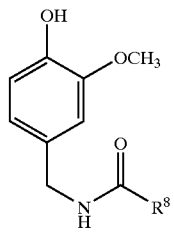

(VII)

wherein $R^8$ represents a straight-chain or branched alkyl or alkenyl group,
such as capsaicin and nonanoic acid vanillylamide;
(v) gingeron, capsicum tincture, and ginger extract.

Other substances that have been described as a warming agent in the background of the present invention can be used.

Of the above recited warming agents preferred are vanillyl ethyl ether, vanillyl propyl ether, vanillyl butyl ether, vanillyl pentyl ether, vanillyl hexyl ether, gingeron, capsicum tincture, and ginger extract. Still preferred are vanillyl butyl ether, vanillyl pentyl ether, vanillyl hexyl ether, and capsicum tincture. Vanillyl butyl ether is the most preferred.

Component (B) is usually used in an amount of 0.000001 to 100 parts, preferably 0.0001 to 10 parts, still preferably 0.001 to 1 part, by weight per part by weight of component (A), and component (C) is usually used in an amount of 0.5 to 100 parts, preferably 0.5 to 10 parts, still preferably 0.5 to 1 part, by weight per part by weight of component (A). Where the warming composition comprises both components (B) and (C), components (B) and (C) are used in an a total amount of 0.000001 to 100 parts, preferably 0.0001 to 10 parts, by weight per part by weight of component (A). The weight ratio of component (C) to component (B) is preferably 0.01 to 100.

A preferred combination of components (A), (B), and (C) includes a combination of (A) 3-(l-menthoxy)propane-1,2-diol or 3-(l-menthoxy)-2-methylpropane-1,2-diol and (B) vanillin and/or (C) vanillyl butyl ether. In this case, the combination usually comprises 0.0001 to 10 parts by weight, preferably 0.01 to 10 parts by weight, of component (B) and 0.5 to 5 parts by weight of component (C) each per part by weight of component (A).

The warming composition, which comprises component (A) and components (B) and/or (C), may be diluted with a diluent safe to a human body, such as ethanol or pure water at an appropriate dilution decided according to the intended use, for example, about 1:2 to 1:10000.

The warming composition can be incorporated into a fragrance composition. The fragrance composition is not particularly limited, and any fragrance composition known in the art is used. Examples of suitable fragrance compositions include, as classified by note, those having a citrus note, a green note, a floral note, an aldehyde note, a fruity note, a woody note, a mossy note, a sweet note, a musky note, an amber note, an animal note, a minty note, a herbal note, and a marine note; and, as classified according to floral essential oils, blackcurrant, boronia broom, capucine, carnation, cassie, champaca, chrysanthemum, clover, cyclamen, freesia, gardenia, helichrysum, heliotrope, honeysuckle, hyacinth, jasmine, karo-karonde, lilac, lily, lily-of-the-valley, linden blossom, magnolia, marigold, mimosa, narcissus, neroli, orange flower, orchid, osmanthus, poppy, reseda, rose, stephanotis, sweet pea, tuberose, verbena, violet, wallflower, wisteria, ylang ylang, lavender, and jonquille. The warming composition of the invention can be used as a blending component or an additive component in blending synthetic or natural fragrance components or as an additive after blending.

The warming composition or the fragrance composition of the invention can be used as an additive component to various products. The content of the warming composition in a final product is subject to wide variation according to the kind of the product, the amount of the product to be applied, the mode of use or application of the product, and the like. In general, the content of each of components (A), (B), and (C) in a final product can range from 0.000001 to 10%, preferably 0.0001 to 1%, still preferably 0.001 to 0.5%, by weight based on the final product. Component (A) and components (B) and/or (C) may be added to a product either separately with or without an appropriate solvent or in the form of a composition previously prepared from the components (i.e., the warming composition or the fragrance composition). They may be added as compounding components in the course of producing the product.

The warming composition can be used in cosmetics, toiletries, bath additives, pharmaceuticals, etc. as a component for providing warmth or as a component for providing a sustained, long-lasting sensation of warmth. Cosmetics and toiletries to which the warming composition is added include, but are not limited to, soaps, body shampoos, shampoos, hair rinses, hair conditioners, hair treatments, antiperspirants, skin lotions, skin creams, moisturizers, deodorants, cologne, perfumes, lipsticks, lip creams, and so forth. The pharmaceuticals to which the warming composition is added include, but are not limited to, applications, such as poultices.

These products can contain various additives in addition to the warming composition of the invention, such as circulation stimulants, antiinflammatory agents, humectants, astringents, antibacterial and/or antifungal agents, inorganic salts, organic salts, oily components, surface active agents, crude drugs, pigments, perfumes, sulfur, sinter deposit, bactericides, and so forth.

The products containing the warming composition of the invention are described more specifically with particular reference to external application for skin, such as cosmetics, and bath additives.

External applications for skin, such as cosmetics, can contain the warming composition in an arbitrary amount, for example, 0.00001 to 10%, particularly 0.001 to 1%, by weight based on the total preparation.

The external application for skin of the present invention can further contain, in addition to the warming composition, powders commonly used in cosmetic formulations, such as inorganic powders and organic powders (e.g., homopolymers, copolymers, resins). Preferred of them are talc, sericite, mica, kaolin, silicone resin, and nylon for their good feel.

It is preferred for the powder to have an average particle size of 0.1 to 15 $\mu$m, particularly 1 to 10 $\mu$m. From the standpoint of feel on use, the powder is preferably added in an amount of 1 to 60% by weight, particularly 5 to 25% by weight, based on the external application for skin.

The external application for skin of the present invention can further contain oily substances. Oily substances that are preferred for feel on use include avocado oil, tsubaki oil, turtle oil, corn oil, olive oil, wheat embryo oil, soybean oil, jojoba oil, peanut oil, cacao butter, lanolin, liquid paraffin, squalane, squalene, vaseline, cholesteryl esters, and silicone oil.

Of these oily substances preferred for the feel on use are those having a surface tension of 30 dyn/cm or less at 25° C., particularly silicone oil, such as methylpolysiloxane, dimethylpolysiloxane, methylcyclopolysiloxane, diethylpolysiloxane, methylphenylpolysiloxane, fatty acid-modified polysiloxane, higher alcohol-modified polysiloxane, and amino-modified polysiloxane. In particular, methylpolysiloxane and dimethylpolysiloxane are preferred. The most preferred are those having a viscosity of 200 centistokes (cs) or less at 25° C. for their effects on improving the feel on use.

A preferred content of the oily substance in the external application for skin is 0.1 to 20%, particularly 1 to 10%, by weight. In order to secure retention of the powdery component on the skin, the oily substance and the powder are preferably used at a weight ratio of 1:20 to 20:1, particularly 1:1 to 1:10.

The external application for skin can contain alcohols. Preferable alcohols include ethyl alcohol, propylene glycol, 1,3-butylene glycol, glycerol, and sorbitol. The alcohols may be used either individually or as a combination of two or more. From the viewpoint of feel on use, the alcohols are preferably used in an amount of 0.1 to 30%, particularly 1 to 20%, by weight based on the composition.

The external application for skin can further contain physiologically effective humectants, antiinflammatory agents, skin whitening agents, ultraviolet absorbents, bactericides, antiperspirants, perfumes, and the like.

The external application for skin of the invention can have any conceivable form selected according to the site or occasion of application and include, for example, lotions, emulsions, creams, powders, poultices, packs, massaging preparations, gels, pastes, and sprays.

Where the warming composition is incorporated into bath additives, the amount to be added is preferably, but not limited to, 0.000001 to 1%, particularly 0.0001 to 0.1%, by weight based on the total bath additives.

The bath additives is put in bath water preferably in a concentration of 0.00015 to 150 ppm, particularly 0.015 to 15 ppm.

If desired, the bath additives can contain inorganic salts, organic acids, oily components, and the like in addition to the warming composition. The inorganic salts include sodium chloride, sodium hydrogencarbonate, sodium carbonate, borax, sodium sulfate, sodium sulfide, sodium sesquicarbonate, sodium nitrate, sodium thiosulfate, sodium polyphosphate, sodium phosphate, calcium oxide, magnesium oxide, calcium carbonate, magnesium carbonate, potassium chloride, and potassium sulfide. Among them preferred are sodium chloride, sodium hydrogencarbonate, sodium carbonate, sodium sulfate, sodium sesquicarbonate, magnesium oxide, calcium carbonate, and magnesium carbonate. They can be used either individually or as a combination thereof. A total content of these inorganic salts in the bath additives is preferably 5% or more, still preferably 10% or more, by weight.

The organic acids include succinic acid, fumaric acid, malic acid, tartaric acid, citric acid, and benzoic acid. They can be added either individually or as a combination of two or more. A total content of these organic acids in the bath additives is preferably 0.1 to 95% by weight.

The oily components include fats and oils, waxes, hydrocarbons, higher fatty acids, higher alcohols, esters, essential oils, and silicone oils.

The bath additives can further contain other ingredients that are customarily employed in the art. Specific but non-limiting examples of useful ingredients of the bath additives are:

(a) inorganic acids, such as boric acid, metasilicic acid, and silicic anhydride;

(b) crude drugs, such as fennel, chamomillae flos, ginkgo, phellodendron, cinnamon bark, catharmi flos, paeonia radix, ginger, calamus, cnidii rhizoma, angelicae radix, orange peel, Atractylodis Lanceae rhizoma, valerianae radix, bitter orange peel, Japanese mint (*Mentha arvensis*), hoelen, ginseng radix, and oat, and their extracts;

(c) pigments, such as coal tar dyes of Positive Lists I and II as laid down in Ministry of Health, Labor and Welfare Ordinance No. 30, such as yellow No. 4, blue No. 1 and yellow No. 202(1), and natural pigments permitted as food additives, such as chlorophyll, riboflavin, crocin, safflower, and anthraquinone;

(d) vitamins, such as vitamin A, vitamin C, vitamin d, and vitamin E;

(e) fragrances; and (f) others, such as sulfur, sinter deposit, mineral sand, mica powder, neutral white clay, roasted rice bran, bactericides, antiseptics, and other ingredients necessary to make preparations.

The bath additive is prepared by adding to the warming composition arbitrary ingredients chosen from the above-described substances according to necessity. The content of these arbitrary ingredients in the composition can range 0 to 99% by weight. The bath additive composition thus prepared may be stabilized or made into an emulsion by addition of an adequate amount of water within a range of from 0.01 to 90% by weight. Similarly to known bath additives, the bath additives can have any form, such as powders, granules, tablets, and liquids.

The present invention will now be illustrated in greater detail with reference to Examples in view of Comparative Examples, but it should be understood that the invention is not limited thereto. Unless otherwise noted, all the percents are by weight.

Abbreviations used hereunder have the following meanings and particulars of commercially available products used hereunder are also as follows.

CA-10: 3-(l-menthoxy)propane-1,2-diol
TPG-1: 3-(l-menthoxy)-2-methylpropane-1,2-diol
TK-5: 3-(1-Methoxy)ethan-1-ol
VBE: Vanillyl butyl ether
Alscope TAP-30: Sodium polyoxyethylene lauryl ether sulfate (3E.O.) (27%), available from Toho Chemical Industry Co., Ltd.
SWANOL AM-101: 2-Alkyl-N-carboxymethyl-N-hydroxyethylimidazoliumbetaine (40%), available from Nikko Chemicals Co., Ltd.
Poise C-60H: o-[2-Hydroxy-3-(trimethylammonio)propyl] hydroxyethyl cellulose chloride, available from Kao Corporation
Amizol CDE: Coconut oil fatty acid diethanolamide, available from Kawaken Fine Chemicals Co., Ltd.
BHT: 2,6-Di-t-butyl-4-methylphenyl
Texin SS-1: Disodium polyoxyethylene lauryl sulfosuccinate (1E.O.) (42%), available from Cognis Japan Plantaren 2000upnp: Alkyl ($C_{8-16}$) glucoside, available from Cognis Japan.

EXAMPLES 1 TO 11 AND COMPARATIVE EXAMPLES 1 TO 4

Warming Effect in Bath Additives

Thirty grams of a powdery bath additives having the formulation shown in Tables 1 and 2 below was put in 200 l of bath water at 41° C. The warming effect of the bath water was evaluated by a panel consisting of five healthy males and five healthy females in terms of (1) sensation felt (a) immediately after taking a bath, (b) after 1 hour from taking a bath, and (c) after 3 hours from taking a bath and (2) irritation felt during bathing. The sensations were described in comparison with those felt in the bath water of Comparative Example 1 as a control. The results obtained are shown in Tables 1 and 2. In Tables, symbols (a), (b) and (c) in the column of "Effect" have the above-described meanings.

TABLE 1

| Formulation (%) | Example 1 | Example 2 | Example 3 | Example 4 | Example 5 | Example 6 | Example 7 | Example 8 |
|---|---|---|---|---|---|---|---|---|
| Vanillin | 0.01 | 0.01 | 0.01 | 0.01 | 0.01 | — | — | — |
| VBE | — | — | — | — | — | 0.01 | — | 0.0005 |
| Capsicum tincture | — | — | — | — | — | — | 0.01 | — |
| Ginger extract | — | — | — | — | — | — | — | — |
| l-Menthol | — | — | — | 0.01 | — | — | — | — |

TABLE 1-continued

| Formulation (%) | Example 1 | Example 2 | Example 3 | Example 4 | Example 5 | Example 6 | Example 7 | Example 8 |
|---|---|---|---|---|---|---|---|---|
| CA-10 | 0.01 | — | — | — | — | 0.01 | 0.01 | 0.0005 |
| TPG-1 | — | 0.01 | — | — | — | — | — | — |
| TK-5 | — | — | 0.01 | — | — | — | — | — |
| p-Menthane-3,8-diol | — | — | — | — | 0.01 | — | — | — |
| Anhydrous sodium sulfate | 98.45 | 98.45 | 98.45 | 98.45 | 98.45 | 98.45 | 98.45 | 98.45 |
| Silicic anhdride | 0.5 | 0.5 | 0.5 | 0.5 | 0.5 | 0.5 | 0.5 | 0.5 |
| Pigment (yellow No. 202(1)) | 0.05 | 0.05 | 0.05 | 0.05 | 0.05 | 0.05 | 0.05 | 0.05 |
| Fragrance | 0.98 | 0.98 | 0.98 | 0.98 | 0.98 | 0.98 | 0.98 | 0.999 |
| Effect | | | | | | | | |
| Sensation (a) | no difference from control | no difference from control | no difference from control | no difference from control | no difference from control | no difference from control | no difference from control | no difference from control |
| (b) | warmth in the whole body | warmth in the whole body | warmth in the whole body | slight warmth in the whole body | warmth in the whole body | warmth in the whole body | warmth in the extremities | warmth in the whole body |
| (c) | warmth in the whole body | warmth in the whole body | warmth in the whole body | slight warmth in the whole body | slight warmth in the whole body | warms in the whole body | warmth in the extremtities | warmth in the whole body |
| Irritation | no irritation | no irritation | no irritation | no irritation | no irritation | no irritation | a slight itch | no irritation |

TABLE 2

| Formulation (%) | Example 9 | Example 10 | Example 11 | Comp. Example 1 (control) | Compara. Example 2 | Compara. Example 3 | Compara. Example 3 |
|---|---|---|---|---|---|---|---|
| Vanillin | — | 0.01 | 0.01 | — | 0.05 | — | — |
| VBE | — | 0.01 | — | — | — | — | 0.05 |
| Capsicum tincture | — | — | 0.01 | — | — | — | — |
| Ginger extract | 0.01 | — | — | — | — | — | — |
| l-Menthol | — | — | — | — | — | — | — |
| CA-10 | 0.01 | — | — | — | — | 0.05 | 0.05 |
| TPG-1 | — | 0.01 | — | — | — | — | — |
| TK-5 | — | — | 0.01 | — | — | — | — |
| p-Menthane-3,8-diol | — | — | — | — | — | — | — |
| Anhydrous soldium sulfate | 98.45 | 98.45 | 98.45 | 98.45 | 98.45 | 98.45 | 98.45 |
| Silicic anhdride | 0.5 | 0.5 | 0.5 | 0.5 | 0.5 | 0.5 | 0.5 |
| Pigment (yellow No. 202(1)) | 0.05 | 0.05 | 0.05 | 0.05 | 0.05 | 0.05 | 0.05 |
| Fragrance | 0.98 | 0.97 | 0.97 | 1 | 0.98 | 0.95 | 0.95 |
| Effect | | | | | | | |
| Sensation (a) | no difference from control | no difference from control | no difference from control | | no difference from control | no difference from control | slightly warmer |
| (b) | slight warmth in the whole body | warmth in the whole body | warmth in the whole body | | no difference from control | no difference from control | no difference from control |
| (c) | slight warmth in the whole body | warmth in the whole body | warmth in the whole body | | no difference from control | no difference from control | no difference from control |
| Irritation | no irritation | no irritation | no irritation | | no irritation | no irritation | no irritation |

As can be seen from Tables 1 and 2, the bath additives of Comparative Example 2 or 3 which contain (B) vanillin or (A) CA-10 alone produces no effect that could be expected from each component. The bath additives of Comparative Example 4 which contains (C) VBE alone slightly manifests the warming effect of VBE, which lacks long-acting properties. All the bath additives of Examples 1 to 11, which are the warming compositions of the invention, were recognized by all the panel members to produce warming effects.

EXAMPLES 12 TO 15 AND COMPARATIVE EXAMPLES 5 TO 8

Warming Effect in Body Shampoos:

Body shampoos having the formulations shown in Table 3 were prepared. A panel consisting of five healthy males and five healthy females was asked to wash their body with a cotton wash cloth to which 15 g of each body shampoo was applied and to evaluate the warming effect of the body shampoo in terms of (1) sensation they felt (a) immediately after washing, (b) after 1 hour from washing, and (c) after 3 hours from washing and (2) irritation felt during washing. The sensations were described in comparison with those felt with the body shampoo of Comparative Example 5 as a control. The results obtained are shown in Table 3. In Table 3, symbols (a), (b) and (c) in the column of "Effect" have the above-described meanings.

TABLE 3

| Formulation (%) | Example 12 | Example 13 | Example 14 | Example 15 | Comp. Ex. 5 (control) | Compara. Example 6 | Compara. Example 7 | Compara. Example 8 |
|---|---|---|---|---|---|---|---|---|
| Vanillin | — | 0.06 | 0.03 | — | — | — | — | — |
| VBE | 0.1 | — | 0.03 | 0.006 | — | — | — | 0.2 |
| l-Menthyol | 0.05 | — | — | — | — | 0.4 | 0.2 | — |
| CA-10 | 0.05 | 0.06 | 0.06 | 0.006 | — | — | 0.2 | — |
| Triethanolamine | 9 | 9 | 9 | 9 | 9 | 9 | 9 | 9 |
| Lauric acid | 6 | 6 | 6 | 6 | 6 | 6 | 6 | 6 |
| Myristic acid | 9 | 9 | 9 | 9 | 9 | 9 | 9 | 9 |
| Texin SS-1 | 10 | 10 | 10 | 10 | 10 | 10 | 10 | 10 |
| Pantaren 2000 upnp | 8 | 8 | 8 | 8 | 8 | 8 | 8 | 8 |
| Glycerol laurate | 1 | 1 | 1 | 1 | 1 | 1 | 1 | 1 |
| Ethylene glycol distearate | 2.5 | 2.5 | 2.5 | 2.5 | 2.5 | 2.5 | 2.5 | 2.5 |
| Coconut oil fatty acid diethanolamide | 3 | 3 | 3 | 3 | 3 | 3 | 3 | 3 |
| Propylene glycol | 5 | 5 | 5 | 5 | 5 | 5 | 5 | 5 |
| B.H.T. | 0.1 | 0.1 | 0.1 | 0.1 | 0.1 | 0.1 | 0.1 | 0.1 |
| Disodium edetate | 0.1 | 0.1 | 0.1 | 0.1 | 0.1 | 0.1 | 0.1 | 0.1 |
| Methyl paraben* | 0.2 | 0.2 | 0.2 | 0.2 | 0.2 | 0.2 | 0.2 | 0.2 |
| Propyl paraben** | 0.1 | 0.1 | 0.1 | 0.1 | 0.1 | 0.1 | 0.1 | 0.1 |
| Purified water | 45.2 | 45.3 | 45.3 | 45.4 | 45.4 | 45 | 45 | 45 |
| Fragrance | 0.6 | 0.58 | 0.58 | 0.588 | 0.6 | 0.6 | 0.6 | 0.6 |
| Effect | | | | | | | | |
| Sensation (a) | warmth | no difference from control | comfortable warmth | no difference from control | | strong coolness | coolness | warmth |
| (b) | warmth in the whole body | warmth in the whole body | warmth in the whole body | warmth in the whole body | | almost nothing felt | slight coolness | slight warmth |
| (c) | warmth in the whole body | warmth in the whole body | warmth in the whole body | warmth in the whole body | | nothing felt | nothing felt | nothing felt |
| Irritation | slight irritation | no irritation | almost no irritation | no irritation | | strong irritation | weak irritation by menthol | slight by menthol irritation |

It was confirmed that the body shampoos of Examples 12 and 14 exhibit a warming effect immediately after washing, which is attributed to VBE as component (C), and that the sensation of warmth connects to a long-lasting sensation of warmth provided by the present invention. The body shampoos of Examples 13 and 15 provide no particular feeling different from that obtained with the body shampoo of Comparative Example 5 (control) immediately after washing but turned out to make the user feel warm all over the body after a while.

EXAMPLES 16 TO 20 AND COMPARATIVE EXAMPLES 9 TO 12

Warming Effect in Shampoos:

Shampoos having the formulations shown in Table 4 below were prepared. A panel consisting of five healthy males and five healthy females washed their hair with 10 g of each of the shampoos and evaluated the warming effect of the shampoo in terms of (1) sensation felt (a) immediately after shampooing, (b) after 1 hour from shampooing, and (c) after 3 hours from shampooing and (2) irritation felt during shampooing. The sensations were described in comparison with that those felt with the shampoo of Comparative Example 9 as a control. The results obtained are shown in Table 4, in which symbols (a), (b) and (c) in the column of "Effect" have the above-described meanings.

TABLE 4

| Formulation (%) | Example 16 | Example 17 | Example 18 | Example 19 | Example 20 | Comp. Example 9 (control) | Compara. Example 10 | Compara. Example 11 | Compara. Example 12 |
|---|---|---|---|---|---|---|---|---|---|
| Vanillin | 0.1 | — | 0.1 | 0.02 | — | — | — | — | — |
| VBE | — | 0.1 | — | 0.02 | 0.003 | — | — | — | 0.1 |
| l-Menthol | 0.2 | — | — | — | — | — | 0.5 | 0.3 | — |
| CA-10 | 0.2 | 0.2 | 0.2 | 0.02 | 0.003 | — | — | 0.2 | — |
| Poise C-60H | 1 | 1 | 1 | 1 | 1 | 1 | 1 | 1 | 1 |
| Alscope TAP-30 | 40 | 40 | 40 | 40 | 40 | 40 | 40 | 40 | 40 |
| SWANOL AM-101 | 10 | 10 | 10 | 10 | 10 | 10 | 10 | 10 | 10 |
| Amizol CDE | 2 | 2 | 2 | 2 | 2 | 2 | 2 | 2 | 2 |
| 1,3-Butylene glycol | 2 | 2 | 2 | 2 | 2 | 2 | 2 | 2 | 2 |
| Citric acid | 0.35 | 0.35 | 0.35 | 0.35 | 0.35 | 0.35 | 0.35 | 0.35 | 0.35 |

TABLE 4-continued

| Formulation (%) | | Example 16 | Example 17 | Example 18 | Example 19 | Example 20 | Comp. Example 9 (control) | Compara. Example 10 | Compara. Example 11 | Compara. Example 12 |
|---|---|---|---|---|---|---|---|---|---|---|
| Sodium chloride | | 0.1 | 0.1 | 0.1 | 0.1 | 0.1 | 0.1 | 0.1 | 0.1 | 0.1 |
| Methyl paraben | | 0.2 | 0.2 | 0.2 | 0.2 | 0.2 | 0.2 | 0.2 | 0.2 | 0.2 |
| Propyl paraben | | 0.1 | 0.1 | 0.1 | 0.1 | 0.1 | 0.1 | 0.1 | 0.1 | 0.1 |
| Sodium edetate | | 0.1 | 0.1 | 0.1 | 0.1 | 0.1 | 0.1 | 0.1 | 0.1 | 0.1 |
| Purified water | | 43.15 | 43.35 | 43.35 | 43.59 | 43.65 | 43.65 | 43.15 | 43.15 | 43.55 |
| Fragrance | | 0.5 | 0.5 | 0.5 | 0.5 | 0.494 | 0.5 | 0.5 | 0.5 | 0.5 |
| Effect | | | | | | | | | | |
| Sensation | (a) | weak coolness | warmth | weak coolness | weak warmth | no difference from control | | strong coolness | coolness | warmth |
| | (b) | warmth in the scalp | warmth in the scalp | warmth in the scalp | warmth in the scalp | warmth in the scalp | | almost nothing felt | weak coolness nothing felt | slight warmth nothing felt |
| | (c) | warmth in the scalp | warmth in the scalp | warmth in the scalp | warmth in the scalp | warmth in the scalp | | nothing felt | nothing felt | nothing felt |
| Irritation | | almost no irritation | weak irritation | almost no irritation | almost no irritation | no irritation | | strong irritation by menthol | irritation by menthol | weak irritation |

While the shampoo of Example 16 provides a sensation of coolness immediately after shampooing, which is attributed to menthol, it was confirmed that a feeling of warmth then develops and lasts long. It was proved that the shampoo of Example 17 begins to exert a warming effect during shampooing, which is attributed to VBE, and that the warmth connects to the warming effect produced by the present invention which lasts long. Although part of the panel felt weak coolness attributed to CA-10 while they were shampooing, the all members recognized warmth from all over their head to their neck.

EXAMPLES 21 TO 23 AND COMPARATIVE EXAMPLES 13 TO 16

Warming Effect in Lotions:

Lotions having the formulations shown in Table 5 below were prepared. A panel consisting of five healthy males and five healthy females applied 1 ml of each of the lotions of Examples 21 to 23 and Comparative Examples 14 to 16 to one of their armpits and 1 ml of the lotion of Comparative Example 13 (control) to the other armpit and evaluated the former in comparison with the latter in terms of (1) sensation (a) immediately after application or (b) after 1 hour from the application and (2) the irritation felt on application. The results are shown in Table 5, in which symbols (a) and (b) in the column of "Effect" have the above-described meanings.

TABLE 5

| Formulation (%) | | Example 21 | Example 22 | Example 23 | Compara. Example 13 (control) | Compara. Example 14 | Compara. Example 15 | Compara. Example 16 |
|---|---|---|---|---|---|---|---|---|
| Vanillin | | 0.05 | 0.05 | 0.01 | — | 0.1 | — | — |
| Capsicum tincture | | — | — | 0.01 | — | — | — | 0.01 |
| CA-10 | | 0.05 | — | — | — | — | 0.1 | — |
| TPG-1 | | — | 0.05 | 0.01 | — | — | — | — |
| 95% Ethanol | | 45 | 45 | 45 | 45 | 45 | 45 | 45 |
| Purified Water | | 54.8 | 54.8 | 54.8 | 54.9 | 54.8 | 54.8 | 54.89 |
| Fragrance | | 0.1 | 0.1 | 0.1 | 0.1 | 0.1 | 0.1 | 0.1 |
| Effect | | | | | | | | |
| Sensation | (a) | almost nothing felt | almost nothing felt | almost nothing felt | | no difference from control | almost nothing felt | almost nothing felt |
| | (b) | warmth | warmth | warmth | | no difference from control | no difference from control | no difference from control |
| Irritation | | no irritation | no irritation | no irritation | | no irritation | no irritation | no irritation |

As is apparent from Table 5, the lotions of Comparative Examples 14 to 16, which contain vanillin, CA-10 and capsicum tincture, exhibit almost no warming effect, whereas those of Examples 21 to 23 were recognized to exert a warming effect in a minute after application.

The warming composition of the invention which comprises a cooling agent and a warming agent is incorporated into products to make the products exert an appreciable warming effect in such a low concentration at which each component would be ineffective when used individually. The warming composition makes it possible to produce a warming effect with no skin irritation that has not heretofore been attained. Further, the warming effect obtained by the present invention lasts long.

While the invention has been described in detail and with reference to specific embodiments thereof, it will be apparent to one skilled in the art that various changes and modifications can be made therein without departing from the spirit and scope thereof.

This application is based on Japanese patent application No. 2000-376813 filed Dec. 12, 2000, the entire contents thereof being hereby incorporated by reference.

What is claimed is:

1. A warming composition consisting of a cooling agent and a compound represented by formula (I):

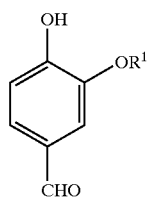

wherein $R^1$ represents a hydrogen atom, a methyl group or an ethyl group, wherein said cooling agent is at least one compound selected from 3-(l-menthoxy)propane-1,2-diol, 3-(l-menthoxy)-2-methylpropane-1,2-diol, p-menthane-3,8-diol, 3-(l-menthoxy)ethan-1-ol, 3-(l-menthoxy)propan-1-ol, and 3-(l-menthoxy)butan-1-ol.

2. Cosmetics, toiletries, bath additives or pharmaceuticals comprising the warming composition according to claim 1.

3. Cosmetics, toiletries, bath additives or pharmaceuticals according to claim 2, wherein the content of said cooling agent and said compound represented by formula (I)

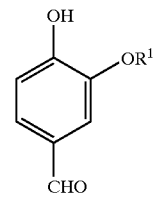

is each 0.001 to 0.5% by weight based on the weight of the total composition, and wherein the compound represented by formula (I) is present in an amount of 0.001 to 1 part by weight per part by weight of the cooling agent.

4. A fragrance composition comprising the warming composition according to claim 1.

5. Cosmetics, toiletries, bath additives or pharmaceuticals comprising the fragrance composition according to claim 4.

6. Cosmetics, toiletries, bath additives or pharmaceuticals according to claim 5, wherein the content of said cooling agent; and said compound represented by formula (I)

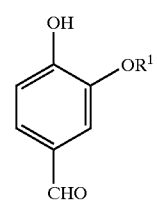

is 0.000001 to 10% by weight based on the weight of the total composition.

* * * * *